US011259716B2

(12) United States Patent
Murray et al.

(10) Patent No.: US 11,259,716 B2
(45) Date of Patent: Mar. 1, 2022

(54) METHOD AND DEVICE FOR RESPIRATORY MONITORING

(71) Applicant: PMD DEVICE SOLUTIONS LIMITED, Cork (IE)

(72) Inventors: Myles Murray, Cork (IE); Stephen Cusack, Cork (IE); Christopher Kinsella, Cork (IE)

(73) Assignee: PMD DEVICE SOLUTIONS LIMITED, Cork (IE)

( * ) Notice: Subject to any disclaimer, the term of this patent is extended or adjusted under 35 U.S.C. 154(b) by 343 days.

(21) Appl. No.: 14/769,044

(22) PCT Filed: Feb. 17, 2014

(86) PCT No.: PCT/EP2014/053048
§ 371 (c)(1),
(2) Date: Aug. 19, 2015

(87) PCT Pub. No.: WO2014/128090
PCT Pub. Date: Aug. 28, 2014

(65) Prior Publication Data
US 2016/0000376 A1    Jan. 7, 2016

(30) Foreign Application Priority Data
Feb. 20, 2013   (IE) ..................................... 2013/0062

(51) Int. Cl.
*A61B 5/08*      (2006.01)
*A61B 5/00*      (2006.01)
(Continued)

(52) U.S. Cl.
CPC .......... *A61B 5/0816* (2013.01); *A61B 5/0826* (2013.01); *A61B 5/113* (2013.01);
(Continued)

(58) Field of Classification Search
CPC ............ A61B 2562/0219; A61B 5/721; A61B 5/1135; A61B 5/6833; A61B 5/113; A61B 5/6805; A61B 2562/0261
See application file for complete search history.

(56) References Cited

U.S. PATENT DOCUMENTS

| 6,517,497 | B2 * | 2/2003 | Rymut ................. | A61B 5/0816 |
| | | | | 600/532 |
| 2005/0119586 | A1 * | 6/2005 | Coyle .................. | A61B 5/0806 |
| | | | | 600/538 |

(Continued)

FOREIGN PATENT DOCUMENTS

| EP | 2417905 A1 | 2/2012 |
| WO | 2009074928 A1 | 6/2009 |
| WO | 2009109903 A1 | 9/2009 |

OTHER PUBLICATIONS

International Search Report; PCT/EP2014/053048; dated Apr. 3, 2014.

*Primary Examiner* — Tse W Chen
*Assistant Examiner* — Michael A Catina
(74) *Attorney, Agent, or Firm* — Renner, Otto, Boisselle & Sklar, LLP

(57) ABSTRACT

A respiration monitoring system has deformation transducers on a flexible substrate arranged to adhere to a patient's torso. A processor receives signals in channels from the transducers and processes them to eliminate, reduce or compensate for noise arising from patient motion artefacts, to provide an output representative of respiration. The transducers have a size and a mutual location on the substrate so that a first transducer can overlie at least part of the 10th rib and a second transducer can overlie at least part of the 11th rib or the abdomen, and the processor processes data from the first transducer as being primarily representative of rib distending respiration and from the second (Continued)

transducer as being primarily representative of either diaphragm respiration or patient motion artefacts.

18 Claims, 11 Drawing Sheets

(51) Int. Cl.
    *A61B 5/113*     (2006.01)
    *G16H 20/40*     (2018.01)
    *G16H 40/67*     (2018.01)

(52) U.S. Cl.
    CPC .......... *A61B 5/6823* (2013.01); *A61B 5/6833* (2013.01); *A61B 5/721* (2013.01); *A61B 5/7207* (2013.01); *A61B 5/7246* (2013.01); *A61B 5/7282* (2013.01); *A61B 5/0022* (2013.01); *A61B 5/0803* (2013.01); *A61B 5/4818* (2013.01); *A61B 5/725* (2013.01); *A61B 5/7225* (2013.01); *A61B 5/7257* (2013.01); *A61B 2560/0285* (2013.01); *A61B 2560/045* (2013.01); *A61B 2560/0412* (2013.01); *A61B 2560/0425* (2013.01); *A61B 2562/0219* (2013.01); *A61B 2562/0261* (2013.01); *A61B 2562/04* (2013.01); *A61B 2562/164* (2013.01); *G16H 20/40* (2018.01); *G16H 40/67* (2018.01)

(56) References Cited

U.S. PATENT DOCUMENTS

2012/0296221 A1   11/2012   Morren
2014/0206977 A1*   7/2014   Bahney ................ A61B 5/6833
                                            600/391

* cited by examiner

METHOD AND DEVICE FOR RESPIRATORY MONITORING

FIELD OF THE INVENTION

The invention relates generally to devices useful in measuring and monitoring respiratory events in a human subject.

PRIOR ART DISCUSSION

Respiratory rate is the measure of the number of breaths a person has per minute and is a key vital sign in human subjects. Spirometry is the measure of lung capacity or lung volume in a human subject. Deterioration of these respiratory functions is the decline or increase of these measures. Measurements outside, or approaching the boundaries of, the predetermined physiological normal values are a pre-indicator to harmful and fatal emerging ailments in human subjects.

Respiration is the process by which living organisms take in oxygen and convert it to energy. Part of this process is the mechanical inhalation of air which, for humans, is done via the nose and mouth. The mechanical respiratory effort is produced by the muscles of respiration. These muscles aid in both inspiration and expiration. The muscle groups which make up this collection include the diaphragm, external intercostal, and internal intercostal muscles. This process is known as respiratory effort, and it is enabled by either or both of:

a) The partial or total displacing of the rig cage (hereafter referred to as rib breathing) upwards and outwards by the external and internal intercostal muscles, along a fixed locus, to produce a vacuum inside the thoracic cavity, thus drawing air into the lungs to enabling respiration to occur, b) The diaphragm pushing down into the abdominal region (hereafter referred to as diaphragm breathing) forcing the abdominal organs to distend outward and thus producing a vacuum in the thoracic region by increasing the volume in the abdominal region.

The above movements may be referred to as distending the rib cage.

A reason for the respiratory rate or capacity of the lung of a patient to fluctuate over a period of time, where physical activity is not considered, can be the result of physiological changes in the health of the patient. Infections in the body can result in a fever and higher heart rate. An infection also produces an increase in respiratory effort, and could be viral or bacterial, or as a result of the environment or complications resulting from medication or surgery. Pneumonia, chronic obstructive pulmonary disease (COPD), and sepsis are all ailments representative of the above and can be indicated by fluctuating respiratory function. This may express either as an alteration of the respiratory rate of the patient or the capacity of the patient to draw in air for efficient respiration.

Respiratory rate is a predominant metric in a predicative patient scoring system known as the Early Warning Score (EWS). Chronic patients suffering from lung diseases such as COPD can be monitored over long periods of time by measuring their lung capacity. As lung diseases affect the normal mechanical operation of respiratory effort, measuring the ability of patients to breathe deeply is also a key measure of their deterioration or recovery. The comprehensive measure of respiratory rates enables medical staff to better assess the EWS with high accuracy and intervene sooner.

U.S. 2012/0296221 (Philips) describes a method and apparatus for determining a respiration signal. A single multi-axial accelerometer is positioned on the body. WO2009/074928 (Philips) describes use of ECG electrodes on an elastically deformable bridge, and there is also a strain sensor and an accelerometer.

The invention is directed towards providing a system for respiratory monitoring which is simpler and/or more robust, and/or more reliable than the prior art.

SUMMARY OF THE INVENTION

According to the invention, there is provided a respiration monitoring system comprising:

a plurality of deformation transducers on a flexible substrate arranged to adhere to a patient's torso, and a processor adapted to receive signals from said transducers and to process them to eliminate, reduce, or compensate for noise arising from patient motion artefacts, to provide an output representative of respiration.

In one embodiment, the deformation transducers are elongate and are arranged on the substrate at a mutual acute angle. Preferably, the angle is in the range of 20° to 80°, preferably 25° to 40°, and most preferably in the region of 27° to 33°.

In one embodiment, the transducers have a size and a mutual location on the substrate so that a first transducer can overlie at least part of the $10^{th}$ rib and a second transducer can overlie at least part of the $11^{th}$ rib or the abdomen, and the processor is adapted to process data from the first transducer as being primarily representative of rib distending respiration and from the second transducer as being primarily representative of either diaphragm respiration or patient motion artefacts. Preferably, the deformation transducers are positioned at an acute angle to each other on the substrate, and the processor is adapted to process data from the transducers on the basis that an apex defined by said mutual position is pointed rearwardly and downwardly with respect to a human subject.

In one embodiment, the system further comprises an accelerometer. In one embodiment, the processor is adapted to process an accelerometer output by correlating the degree of motion artefacts with bodily displacement for aiding the process of eliminating motion artefacts and detect cyclical movements.

In one embodiment, the system includes a gyroscope. Preferably, the processor is adapted to process a gyroscope output by enabling the posture of the body to be known to the processor, thus enabling anomalies of the transducers to be accounted for.

In one embodiment, the system comprises a unitary sensor for adhering to a patient's skin, said sensor including the substrate with the deformation transducers, and the processor. In one embodiment, the processor is included in a housing on the substrate with a signal conditioning circuit. Preferably, the processor housing is releasably mounted on the substrate.

In one embodiment, the processor is adapted to communicate wirelessly via an interface to a host processor.

In one embodiment, the deformation transducers include at least two strain transducers. In one embodiment, in the strain transducers are piezoelectric transducers.

In one embodiment, the processor is adapted to detect excessive displacements resulting in over-pressurisation from invasive or non-invasive artificial ventilation machines.

In one embodiment, the processor is adapted to perform signal conditioning by baseline subtraction against an input voltage signal from the transducers, and to further condition the signal using an exponential moving average filter.

In one embodiment, the processor is adapted to trigger an artefact detection algorithm at regular intervals in which signals which are outside the limits of measurement are removed.

In one embodiment, the processor is adapted to execute a time domain algorithm when determining respiration rate.

In one embodiment, the processor is adapted to execute a frequency domain algorithm when determining respiration rate. Preferably, the time domain algorithm checks distances between peaks and troughs in a respirator waveform and derives a respiration rate. In one embodiment, the frequency domain algorithm uses a fast Fourier transform to extract frequency domain information. In one embodiment, the sensor includes an accelerometer and the processor is adapted to execute the frequency domain algorithm to take accelerometer data as a secondary input and to compensate for cyclical interference from the subject or environment such as walking, by extracting frequency domain information from the accelerometer.

In one embodiment, the processor is adapted to detect and compensate for large movements using the accelerometer data.

In one embodiment, the processor is adapted to assume that a deformation waveform is represented by a repeating pattern of peaks and troughs at a rate indicative of the respiratory rate of the subject, and magnitude of a received transducer signal is considered only of importance if said signal becomes so large as to exceed an output limit of the sensor, or so small as to become indistinguishable from noise.

In one embodiment, the processor is adapted to detect apnea events in sleeping subjects. Preferably, the processor is adapted to recognize missing breathing signals as representative of apnea.

In one embodiment, the system further comprises a wireless transceiver and the processor is adapted to transmit to an external device data to display a respiratory rate history of a subject.

In one embodiment, the processor is adapted to receive a unique identifier for a use with a particular subject, and to discontinue or erase said identifier upon removal and/or re-charging for a next use. In one embodiment, the processor is adapted to save a scanned Medical Record Number (MRN) as a unique identifier. In one embodiment, the processor is adapted to automatically apply a temporary identifier upon removal or re-charging.

In another aspect, the invention provides a method of monitoring respiration of a human subject using a system comprising:
- a plurality of deformation transducers on a flexible substrate arranged to adhere to a patient's torso, and
- a processor adapted to receive signals from said transducers and to process them to eliminate, reduce, or compensate for noise arising from patient motion artefacts, to provide an output representative of respiration, the method comprising the steps of adhering the substrate to a human subject and the processor processing signals from the transducers to derive an output representative of respiration of the human subject.

In one embodiment, the substrate is placed so that a first transducer substantially overlies a $10^{th}$ rib and a second transducer overlies a floating rib or the abdomen, and the processor monitors signals from said transducers by treating signals arising from deformation of the first transducer as being representative of rib distending respiration and by treating signals arising from deformation of the second transducer as being representative of diaphragm breathing or a non-respiration artefact.

In one embodiment, the processor automatically decides on what the deformation of the second transducer represents according to a signal from an auxiliary sensing device.

In one embodiment, the auxiliary sensing device is an accelerometer.

DETAILED DESCRIPTION OF THE INVENTION

Brief Description of the Drawings

The invention will be more clearly understood from the following description of some embodiments thereof, given by way of example only with reference to the accompanying drawings in which:—

FIG. 12(a) shows the raw output from a single transducer over a 60 s time period showing the peaks and troughs indicative of normal breathing, in which one movement artefact can be seen as an increase in the signal strength, FIG. 12(b) shows the same signal with baseline correction and smoothing applied, FIG. 12(c) shows the results from an artefact detection function, FIG. 12(d) shows the same signal with the section designated as artefact smoothly removed from the waveform, FIG. 12(e) shows the signal in FIG. 12(d) with peaks and troughs identified by the system's processor, and FIG. 12(f) shows the frequency spectrum of the signal, with the most prominent signal highlighted at approximately 0.25 Hz, or 15 breaths per minute;

FIG. 14(*b*) shows the signals from an accelerometer housed in the electronics housing for the same period, again having a normalised numerical vertical axis and a time horizontal axis.

DESCRIPTION OF THE EMBODIMENTS

Figure 1:
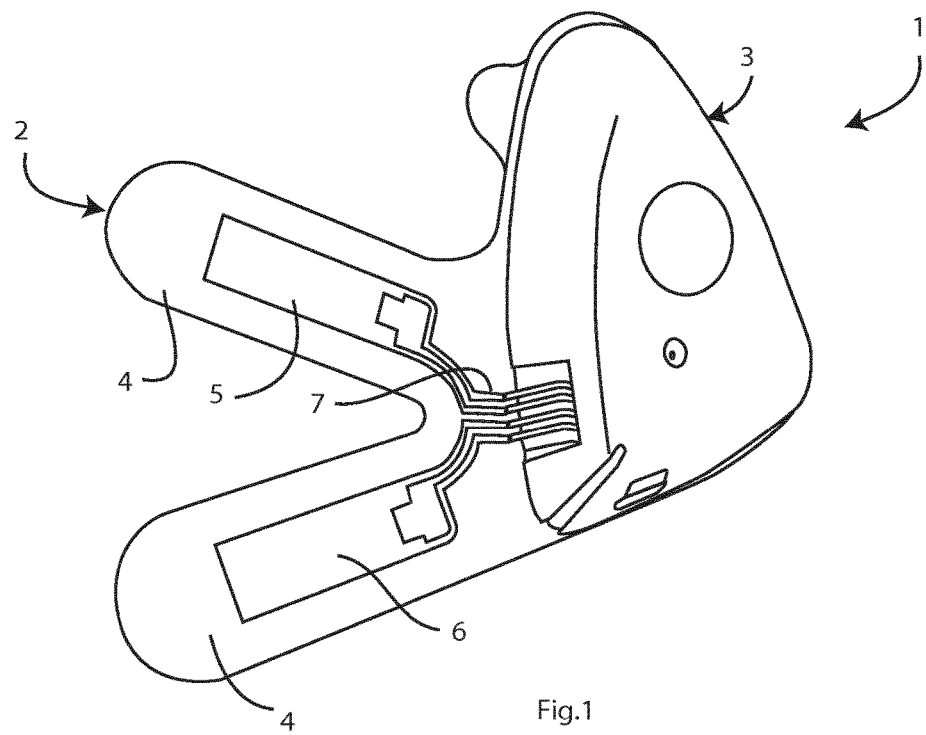
FIG. 1 is a perspective view of a sensor of a system of the invention.
Figure 2:
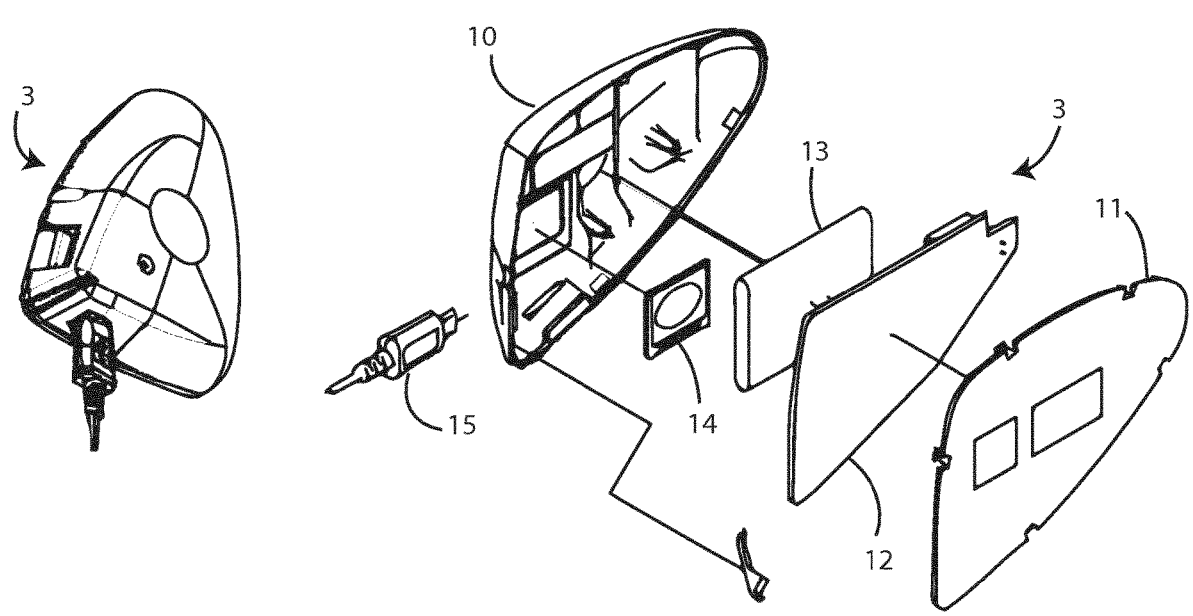
FIG. 2 is an exploded view of a re-usable part.

Referring to FIGS. 1 and 2 a monitoring system comprises a sensor 1 with a disposable substrate 2 for adhering to a patient torso and a re-usable electronics controller 3 adhered to the substrate 2. The substrate 2 comprises a body 4 within which are embedded elongate transducers 5 and 6 for measuring deformation. These are linked by conductors 7 to the controller 3. A sensor system includes the sensor 1 and also a host processor linked by cable or wirelessly, and this may in turn communicate with a remote server.

The controller 3 comprises a plastics housing with a top part 10 and a base 11, containing a circuit board 12 and a rechargeable battery 13, and an alarm sounder 14. There is a connector 15 for wired connection to an external device or host system, although the circuit 12 is also Bluetooth enabled for wireless communication with such a device or system.

The controller 3 is mechanically joined to the substrate 2 by use of an industrial grade hook and loop fastener with the hook side on the side of the controller 3 and the loop side on the consumable substrate 2. This construction allows for durable attachment of the device. It further allows removal of these two elements which is useful in a medical application where consumable body contact sensors are desired to be for single patient single use.

Figure 3:
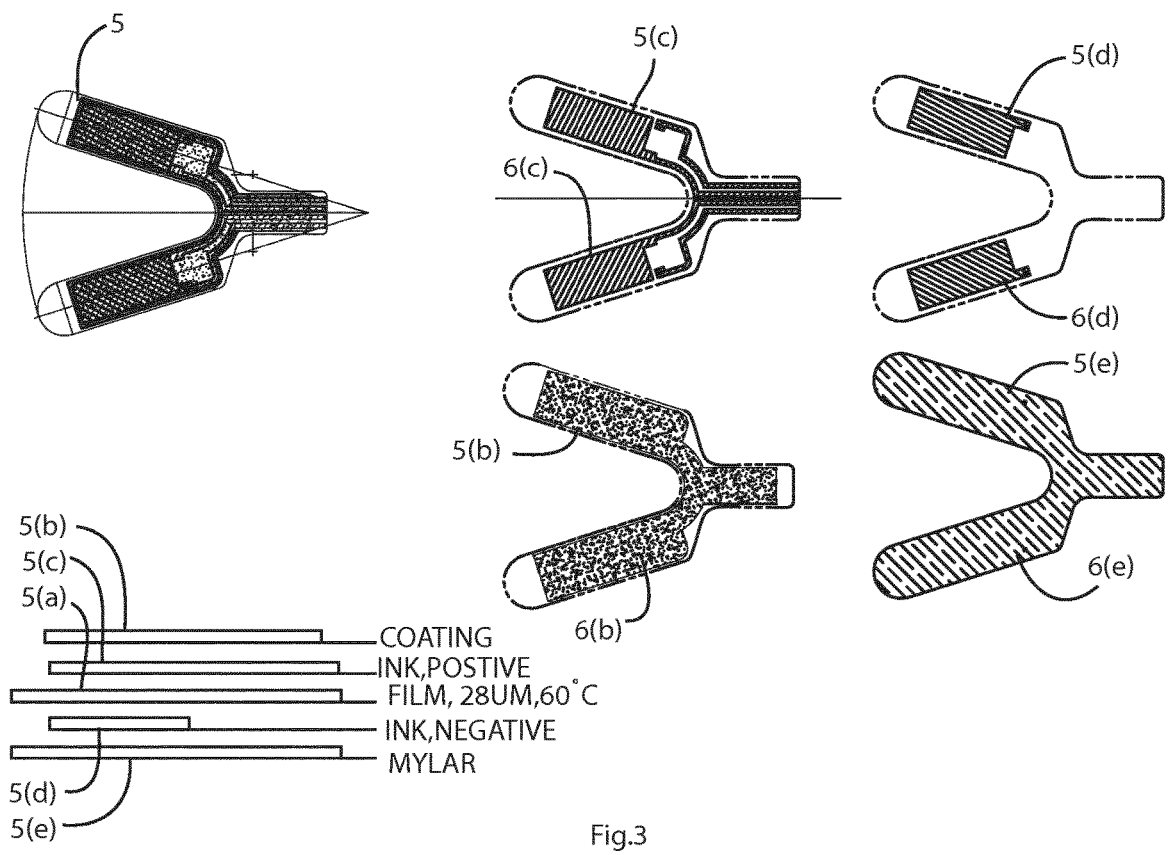
FIG. 3 is a set of views of layers of the transducers.

Referring in particular to FIG. 3 the transducers 5 and 6 comprise a piezoelectric film 5(*a*), 6(*a*) sandwiched between:
- a coating ink pattern 5(*b*), 6(*b*) and a positive ink pattern 5(*c*), 6(*c*), on top; and
- a negative ink pattern 5(*d*), 6(*d*) and a Mylar layer 5(*e*), 6(*e*) underneath.

The composition of the transducer is therefore a multi-layer piezo stack separated by a metal foil. In this embodiment the piezo stack is a multi-purpose, piezoelectric transducer for detecting physical phenomena such as vibration or impact or general deformation. The piezo film element is laminated to the sheet 5(*e*) of polyester (Mylar), and produces a useable electrical signal output when forces are applied to the sensing area.

This compositional stack is heat-laminated using a translucent polymer. Each piezo film layer is partially extended to form a terminal by which a clamp is fixed to. This provides a secure electrical contact for the instrumentation amplifier circuitry.

Figure 4:
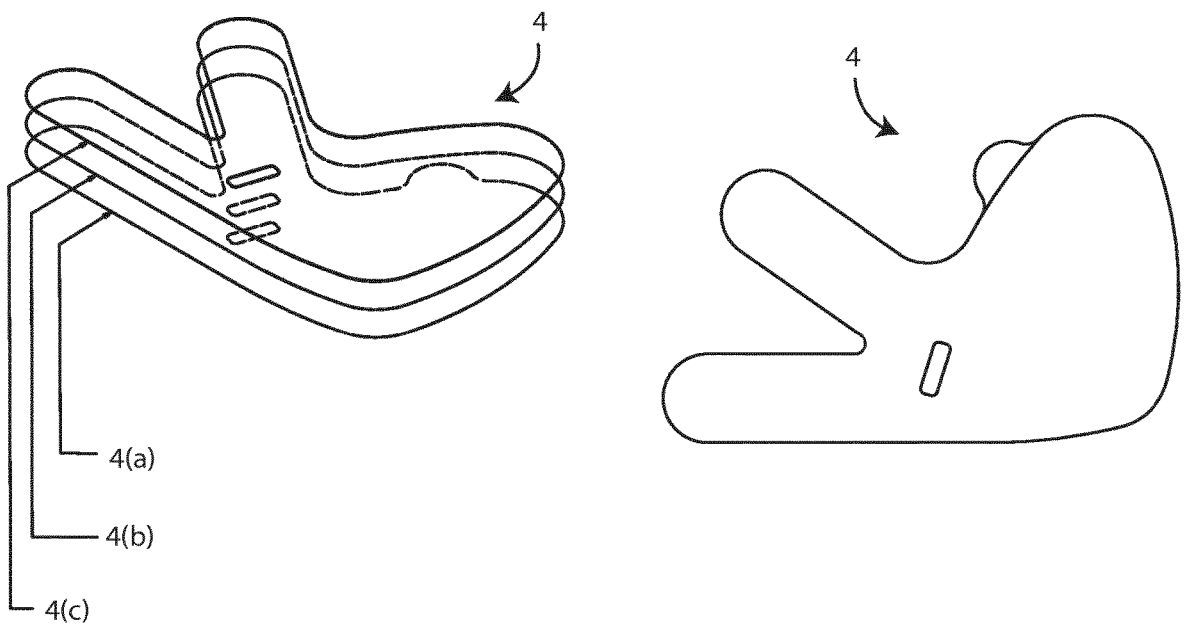
FIG. 4 is an exploded perspective view of the layers of the sensor's substrate.

The substrate body 4 is shown in most detail in FIG. 4. It comprises polypropylene clear release film 4(*a*), 3M™ medical grade silicone adhesive 4(*b*), and a polyester layer 4(*c*). The transducers 5 and 6 are located between the adhesive 4(*b*) and the polyester 4(*c*) layers.

Figure 5:
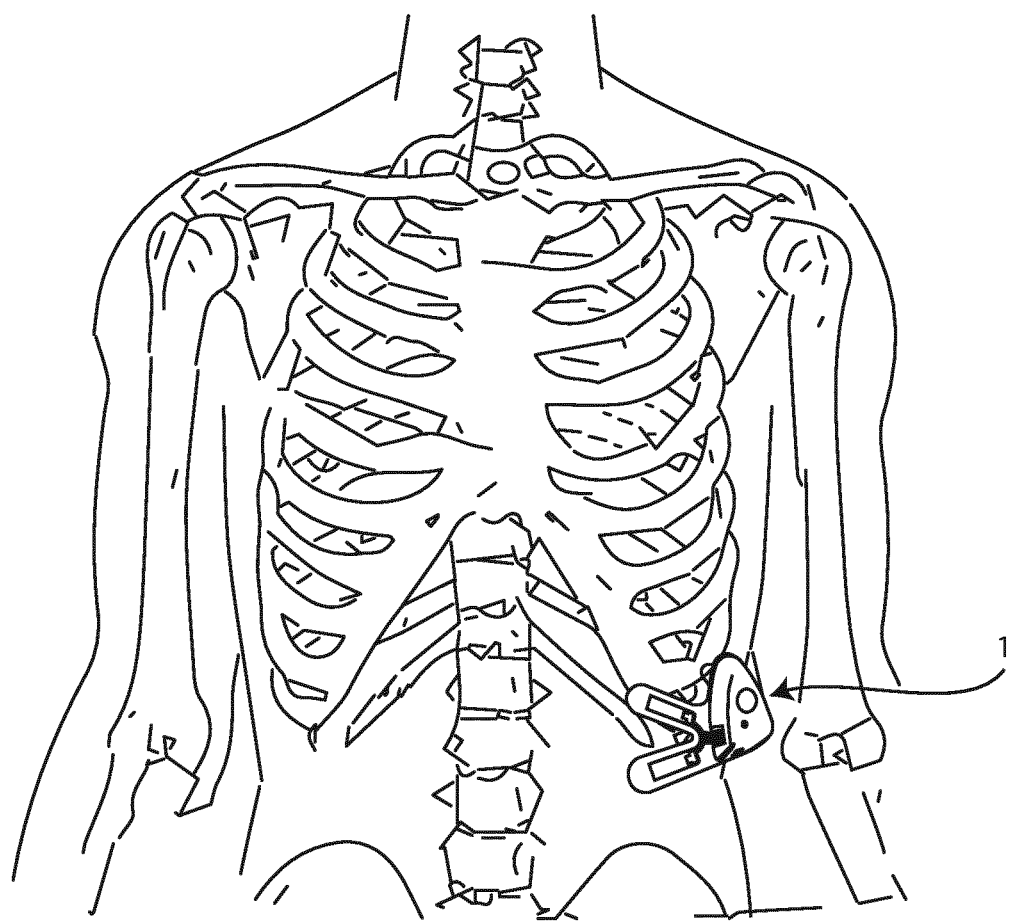
FIG. 5 is a diagram showing an optimal position for the sensor on the body.

As shown in FIG. 5, the sensor may in one embodiment be placed so that the top transducer 5 is over the $10^{th}$ rib, which is the lowermost fixed rib. This leaves the lower transducer 6 in the vicinity of the $11^{th}$ rib, which is floating. Thus, the transducer 6 is effectively over the abdomen and is not affected by the ribs. This is described in more detail below.

Figure 6:
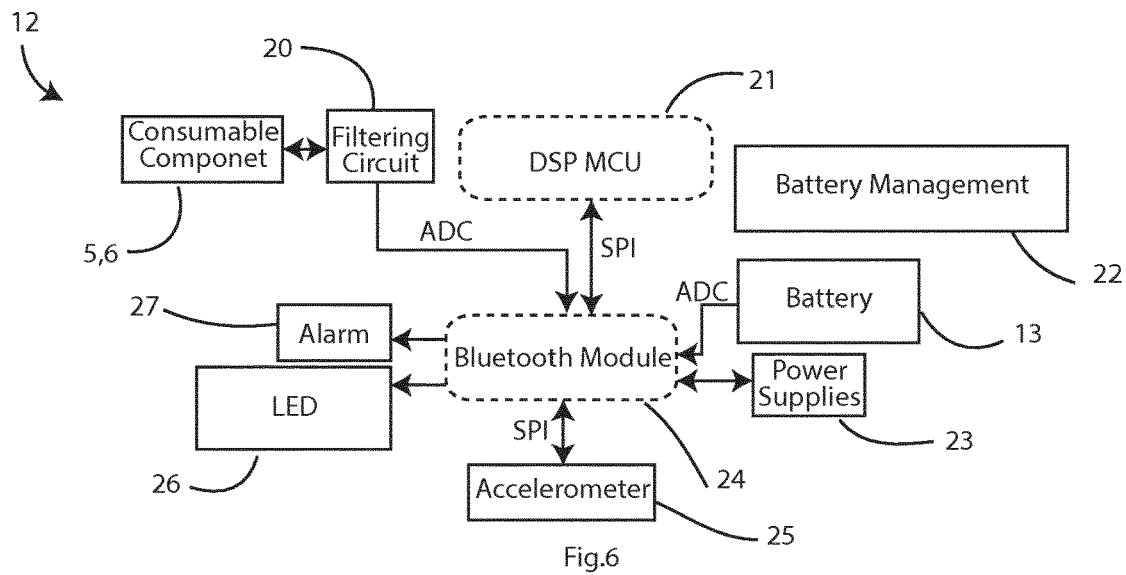
FIG. 6 is a block diagram of the sensor system.

Referring to FIG. 6, at a block diagram level the sensor 1 comprises the transducers 5 and 6 feeding a filtering circuit 20, and an ADC (not shown) feeds a Bluetooth module 24. There is a DSP processor 21 also linked with the Bluetooth module 25. A battery management circuit 22 is linked with the battery 13, and there battery charging terminal 23. The controller 3 houses an accelerometer 25, and there are LED and alarm sounder output devices 26 and 27.

The two transducers 5 and 6 are of equal length, width, thickness, and composition. They are positioned 30° apart from one another about a single point of common placement which ensures a preferred form factor. This preferred configuration is not the only configuration at which this invention will be effective. The angle between each transducer can be different and indeed they may be parallel. However the preferred range is 25° to 55°, and the most preferred is in the region of 27° to 33°. The preferred length and width of each transducer is in the range of 30 mm to 50 mm and 50-400 µm thick.

The transducers 5 and 6 provide the deformation information as described below to allow the processor 21 to automatically generate an output indicating patient respiration. However, the accelerometer 25 allows improved effectiveness in analysing signals arising from wearer's activity and posture. Such variables of posture and activity have direct influence upon the effectiveness of the system. The system can also identify how quickly the human subject is moving, and the subject's posture and when movement based artefacts have been induced in the strain transducer signal. This further enables the human subject to live a normal functional life while the device comprehensively measures the respiratory performance without imposing limitations.

The sensor 1 may be positioned for example over the $9^{th}$ to $11^{th}$ rib, with the controller 3 approximately situated under the subject's arm. The vertical position is determined with reference to the subject's $10^{th}$ rib, with the transducer 5 being preferably situated on or just below the $10^{th}$ rib and in line with this rib. The transducer 6 would therefore be adhered to the subject's abdomen. The transducer 6 is preferably horizontal, but subject physiology may require the transducer 6 to be placed at an angle. The apex of the angle should point towards the rear of the subject. FIG. 5 shows the sensor 1 mounted on the patient's skin at one side. However, the sensor could alternatively be on the opposite side in a mirror-image fashion.

The transducer 5 is particularly responsive to a distending movement of the rib cage, forwardly and laterally. This is almost entirely due to respiration. There may also be pivoting out of the plane of the page in FIG. 5, primarily due to motion artefacts such a walking. Importantly, the transducer 5 is approximately equally responsive to rib distending and motion artefacts, whereas the transducer 6 is less responsive to rib distending and equally responsive to the motion artefacts. When the subject changes their posture, and/or begins breathing under a different regime (normally chest breathing or diaphragm breathing) the signal expressed on the transducers 5 and 6 can change greatly. Typically the transducer 5 which is resting on the rib responds with greater magnitude when the subject is upright and/or breathing mostly using chest movements. When the subject is lying and/or diaphragm breathing the transducer 6, resting on the abdomen, typically responds more strongly. In atypical cases, for instance when the subject is breathing heavily using the ribs, the respiratory response from a transducer can be of such small magnitude as to be indistinguishable from background noise. In this event, the data from this transducer or 6 is discarded, and the other transducer is used solely to derive the respiratory rate.

Different subjects show different signals on transducers for the same posture due to emphasis on gut or rib breathing, and variations in placement. It is not possible to guarantee the patient's position with transducers. The accelerometer 25 helps to determine the orientation of the patient, and the processor compensates the transducer outputs according to information from the accelerometer 25.

The system may be used for monitoring respiratory performances in a clinical environment, or alternatively in a non-clinical environment such as physical exercise monitoring for sports performance enhancement.

The system may be used for the monitoring of apnea events in sleeping subjects. Small configuration changes to the sensor will allow for apnea monitoring. Examples of such alterations include algorithm emphasis on detecting missing breathing signals, or modification of the software to produce a waveform for use in diagnosis by a medical professional.

Regarding data processing and communication, in one configuration, the Bluetooth (BT) module 24 is replaced with a removable hard disk. In another configuration the BT module 24 constantly streams the breathing waveforms, and processing is carried out on a desktop PC or other computer. In instances where healthcare professionals wish to monitor the produced signals directly, limited algorithms can be implemented to clean up the respiratory signal for presentation.

A Bluetooth module 24 is used to communicate with an external device to display the respiratory rate history of the wearer. To ensure continuity of service, on attachment, the BT module is renamed with the patient's Medical Record Number (MRN), for example as scanned from a patient records barcode. The renaming is temporary and lasts for the duration of the device attachment to the patient. Upon removal or recharging, the BT module is automatically renamed to its default identifier. The renaming of the BT module 24 with the MRN allows any authorised device to interact with the sensor 1 for the duration it is attached to the patient.

In instances where the patient can be assumed to be in a steady position e.g. short time spent lying down, signals from a single transducer can suffice to record respiratory rate. However, the multi-transducer configuration covers the full spectrum of patient postures and rib/diaphragm breathing.

In more detail, the signals from both transducers 5 and 6 are filtered and the signal is processed to extrapolate the true wanted signal. This arrangement achieves both filtering and analytical processing capability at the point of measurement. It achieves this with very little restriction in patient movement. Also, some of the components, such as the signal conditioning circuits 20 and the processor 21 are local on the sensor 1. Such a sensor can also be more robust in terms of its application to different physiological parameters e.g. body mass index, body position, location, activity and/or similar parameters. The inclusion of the accelerometer 25 in the device allows such well known art as fall detection, step detection and orientation monitoring to be easily incorporated into the sensor 1. The preferred location for an accelerometer is in the reusable electronic circuitry unit, preferably integrated into the processing circuit 16. The exact placement of the accelerometer is of little importance, as the accelerometer is used to detect gross movement of the subject's body.

The sensor 1 does not have electrical wires which might interfere with the patient. Also, the sensor 1 has a low-profile construction so as not to interfere with the natural movement of the arms of the patient, with an ergonomically efficient design. The sensor is designed to be wearable for a period of up to 8 days. During this period, the device continuously collects and processes data from the transducers and when interrogated by the supervising medical professional report on the subjects respiratory rate over the proceeding number of hours.

Figure 7:
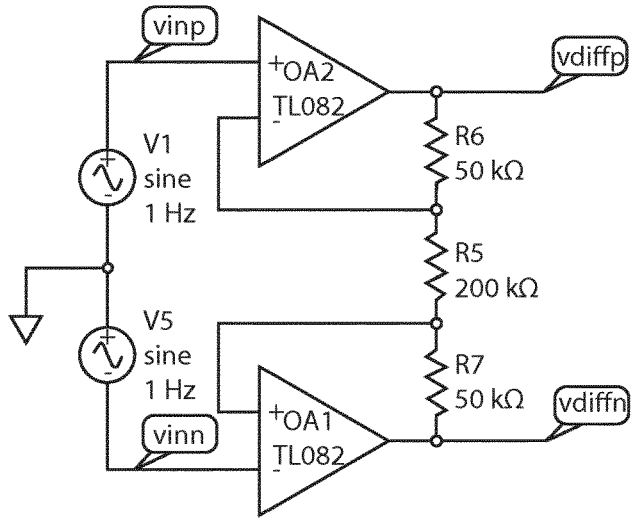
FIG. 7 shows an instrumental amplifier circuit to create a high common-mode rejection and high gain to eliminate any mutual environment interference and boost the signal for processing respectively for a single transducer.

FIG. 7 shows an instrumentation amplifier which amplifies the signals arriving from a single transducer for later processing.

Figure 8:
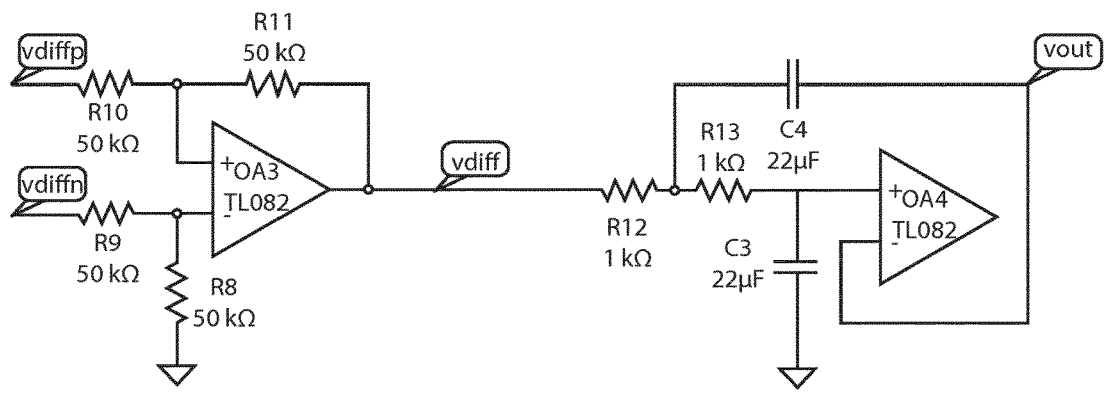
FIG. 8 shows low pass filtering circuitry to produce a single output (per sensor) for digital signal processing, with high frequency components removed, for a single transducer embodiment.

FIG. 8 shows a difference amplifier followed by a $2^{nd}$ order low pass filter. The difference amplifier removes the reference voltage from the incoming signals and amplifies the signal by a gain of one. The low pass filter removes higher frequency signals from the sensor signal.

Figure 9:
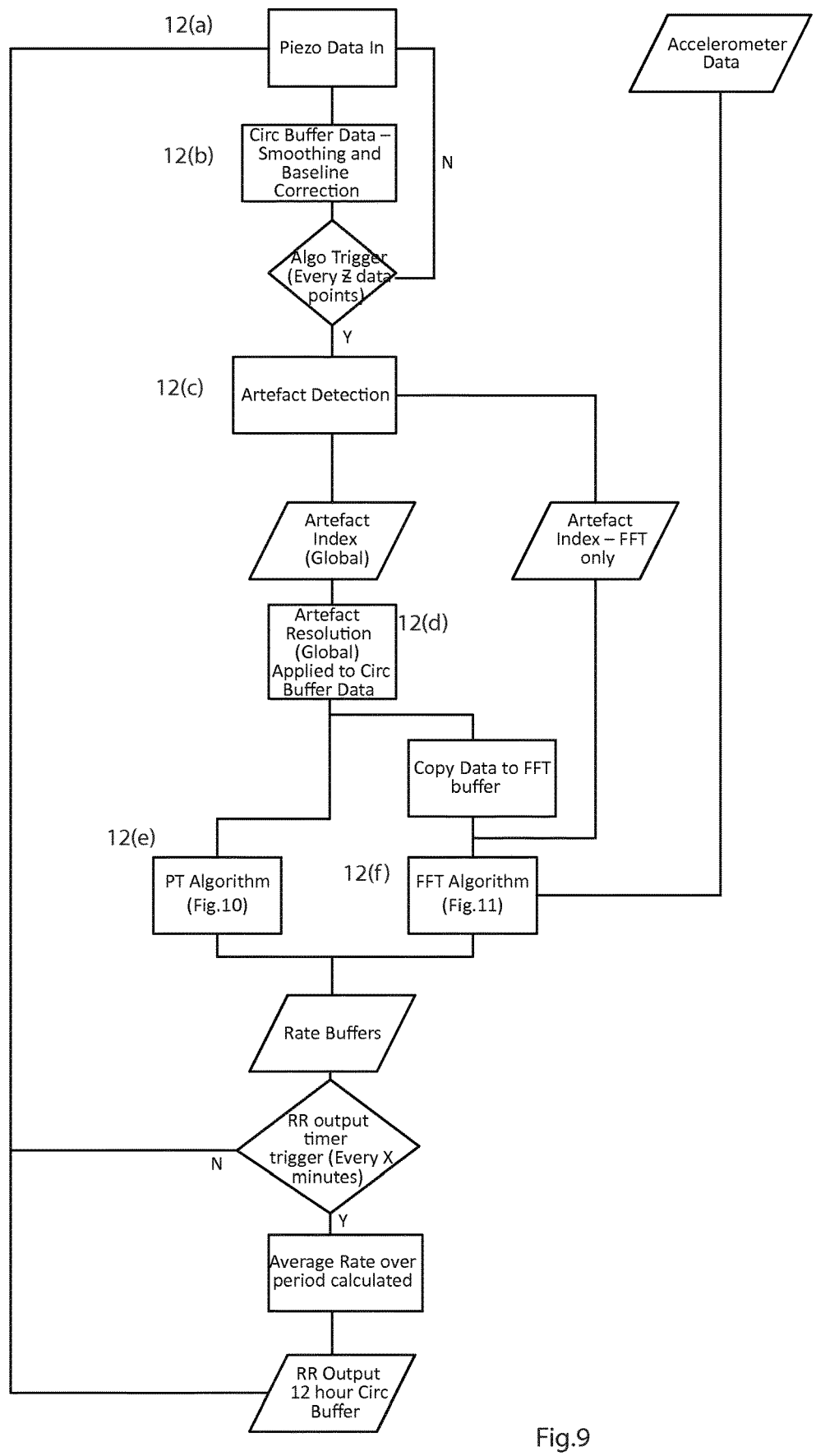
FIG. 9 is a flowchart outlining an algorithm used to process the sensor outputs to generate a respiratory rate.
Figure 10:
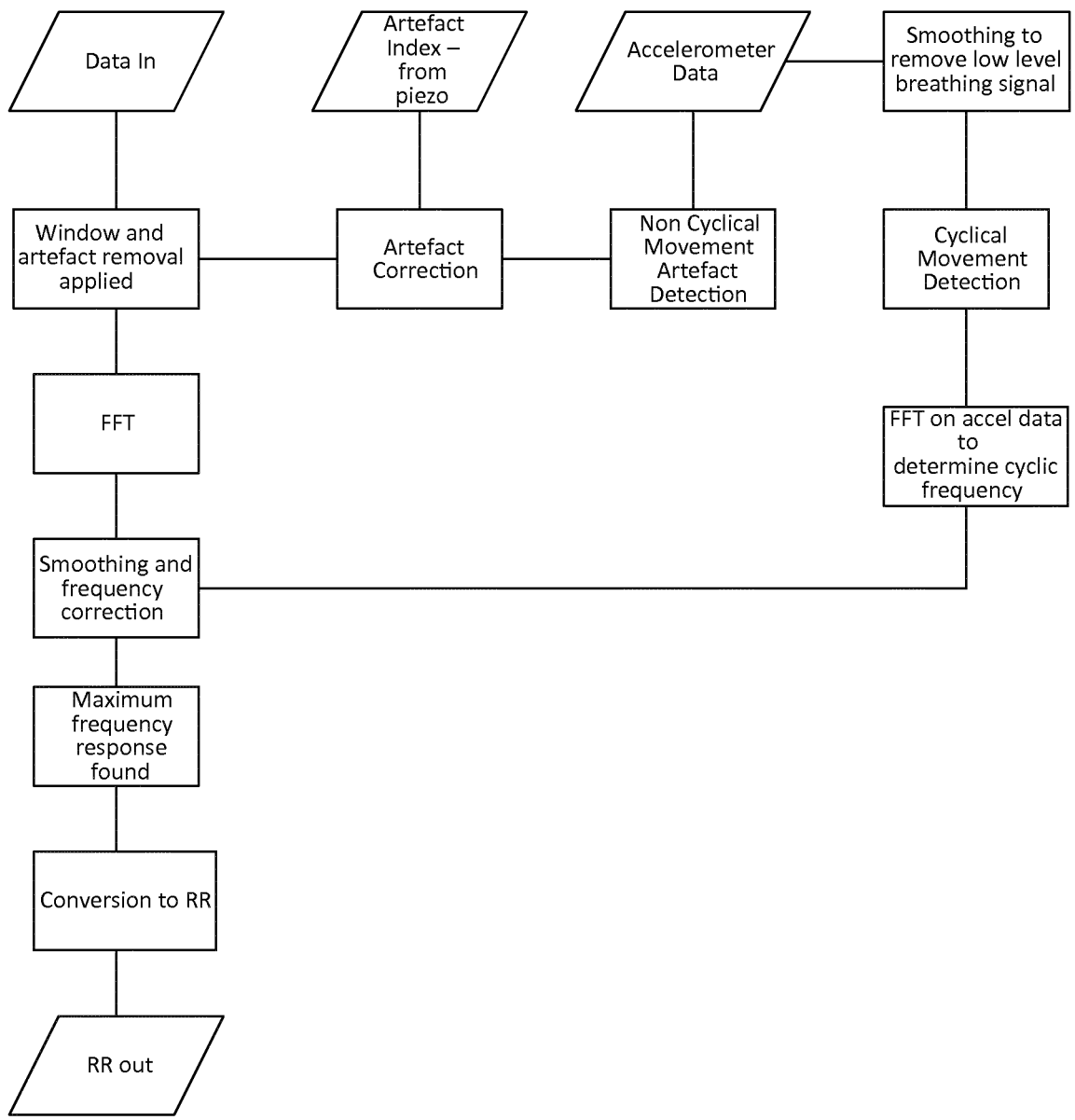
FIG. 10 is a flowchart detailing the use of a Fast Fourier Transform as part of the algorithm in FIG. 9.
Figure 11:
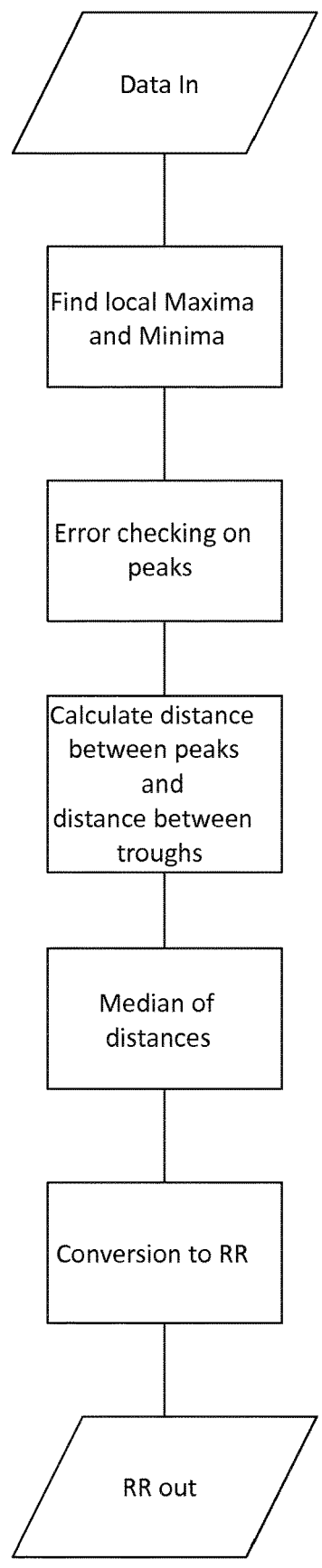
FIG. 11 is a flowchart detailing the use of a time domain algorithm as part of the algorithm in FIG. 9.

The signal processing of the outputs of the movement transducers 5 and 6 and the accelerometer 25 is explained in more detail in FIGS. 9, 10 and 11. The plots of FIGS. 12(*a*) to 12(*e*) are generated at the blocks in FIG. 9 as indicated. Sensor inputs are connected into the microprocessor where all digital analytics are calculated. At this stage digital signal conditioning is performed. This is required supplementary to analogue filtering so as to reduce the effect of aliasing and spurious noise. Filtering in the digital domain provides a richer and more versatile filtering process than what can be achieved in the analogue domain.

Once acquired, the incoming signals are processed to calculate the respiratory rate of the subject over a given time period. Several main algorithm steps are used for the reliable calculation of rates in the presence of movement or other artefacts; signal conditioning, artefact detection, artefact resolution, respiration rate derivation, as well as other miscellaneous supporting algorithms. Rate detection algorithms were noted to fall into two main categories; time domain analysis and frequency domain analysis. Time domain analysis includes techniques such as peak and trough detection, template matching and machine learning. Frequency domain analysis includes techniques such as the discrete Fourier transform, wavelet analysis and auto- and cross-correlation techniques. Algorithms can include inputs from the on-board accelerometer or gyroscope.

One implementation of an analysis algorithm is outlined in FIG. 9. This implementation is given by way of example only, and does not limit the invention to the use of other algorithms, or sub-algorithms. This algorithm is optimised for low power consumption and uses the accelerometer 25 data in addition to the deformation transducers 5 and 6 to derive a clean, conditioned respiratory rate. Signal conditioning is carried out by baseline subtraction against the input voltage signal. The signal is further conditioned using an exponential moving average filter to smooth the signal. When the algorithm is triggered, every 25 s, an artefact detection protocol is triggered. Artefacts detected on the piezoelectric transducer signal (for example, signals which are 'railing', or outside the limits of measurement) are them removed from the signal by smoothly bringing the signal to zero in these areas. Two separate respiratory rate algorithms are then run—one a time domain algorithm and one a frequency domain algorithm. The first concentrates on looking at the distance between the peaks and troughs in the respirator waveform and deriving a rate for that. This is outlined in FIG. 11. The second uses a fast Fourier transform to extract frequency domain information from the waveform, shown in FIG. 10. This algorithm also takes the accelerometer data as a secondary input. Cyclical interference from the subject or environment, e.g. walking, is compensated for by extracting frequency information from the accelerometer. Large movements are also detected and compensated for using the accelerometer data. Once the rate calculations are made, the extracted rates are buffered for communication via Bluetooth to an external tablet PC.

Signals output from the sensor transducers differ greatly from subject to subject and when changes in posture or breathing regime occur. This includes changes in signal strength, changes in the shape of the repeated breathing pattern, and the relative strength of the signals from each of the strain transducers. The implemented algorithm only assumes that the respiratory signal is represented by a repeating pattern of peaks and troughs at a rate indicative of the respiratory rate of the subject, as shown in FIGS. 12 and 13 and 8. The magnitude of the sensor output is considered only of importance if the signal becomes so large as to exceed the output limit of the sensor, or so small as to become indistinguishable from noise. The shape of the repeating signal is not considered to be indicative of any breathing regime. The magnitude and shape of the repeating pattern can change greatly depending on posture, device positioning and subject to subject variation. For these reasons, embedded algorithms have been selected so the sensor does not require that the unit be calibrated for any individual subject.

Figure 12A:
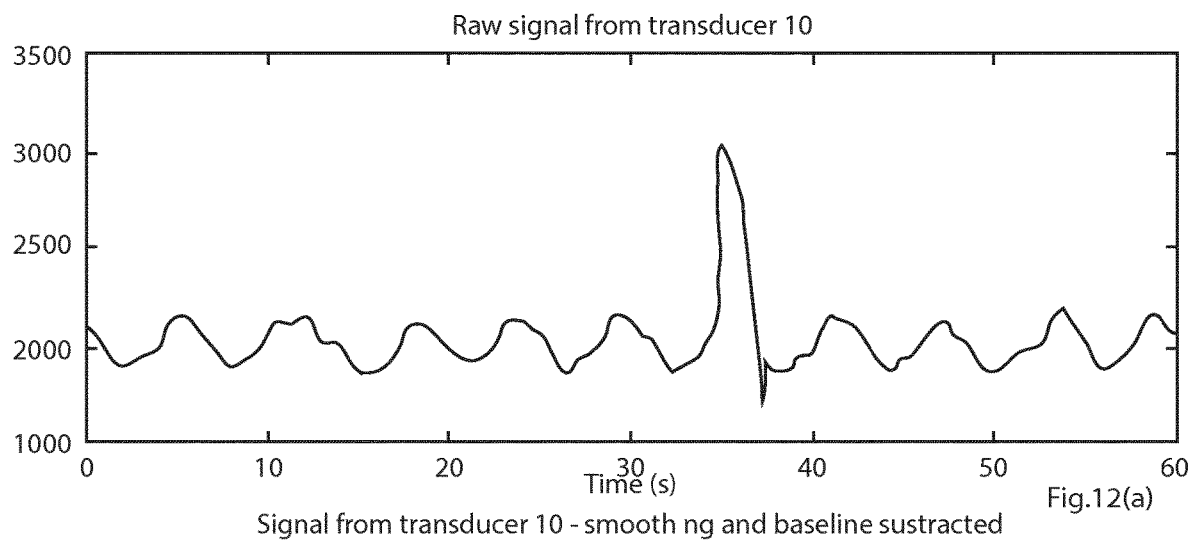
FIGS. 12(a) to 12(f) are plots, having a normalised numerical vertical axis and a time horizontal axis, showing various transducer and system signals as follows.
Figure 12B:
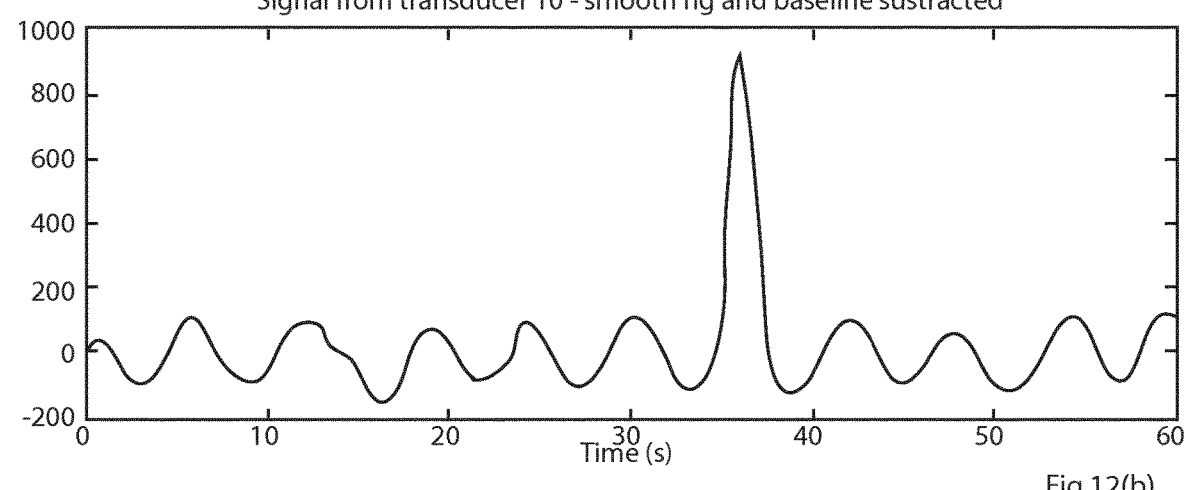
Figure 12C:
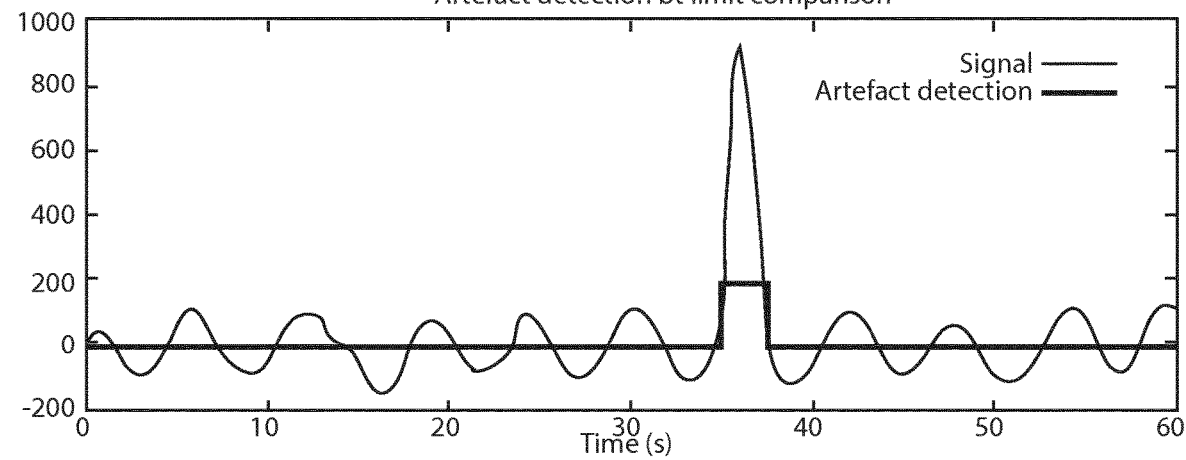
Figure 12D:
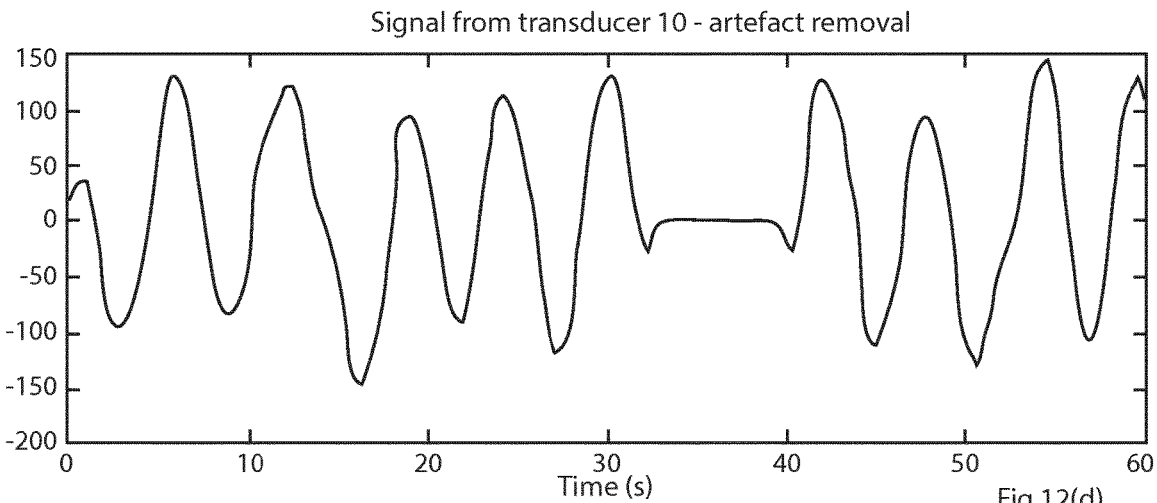
Figure 12E:
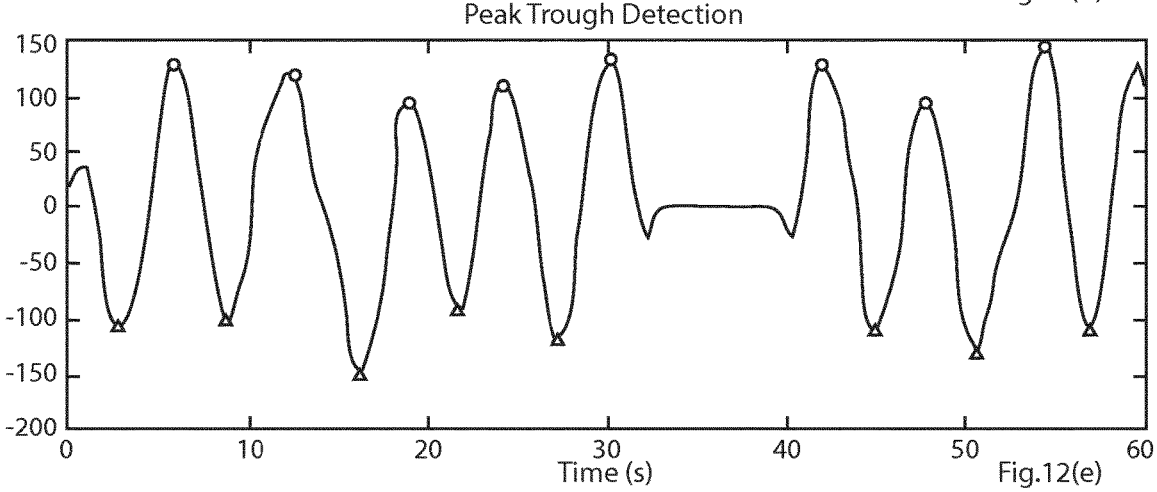
Figure 12F:
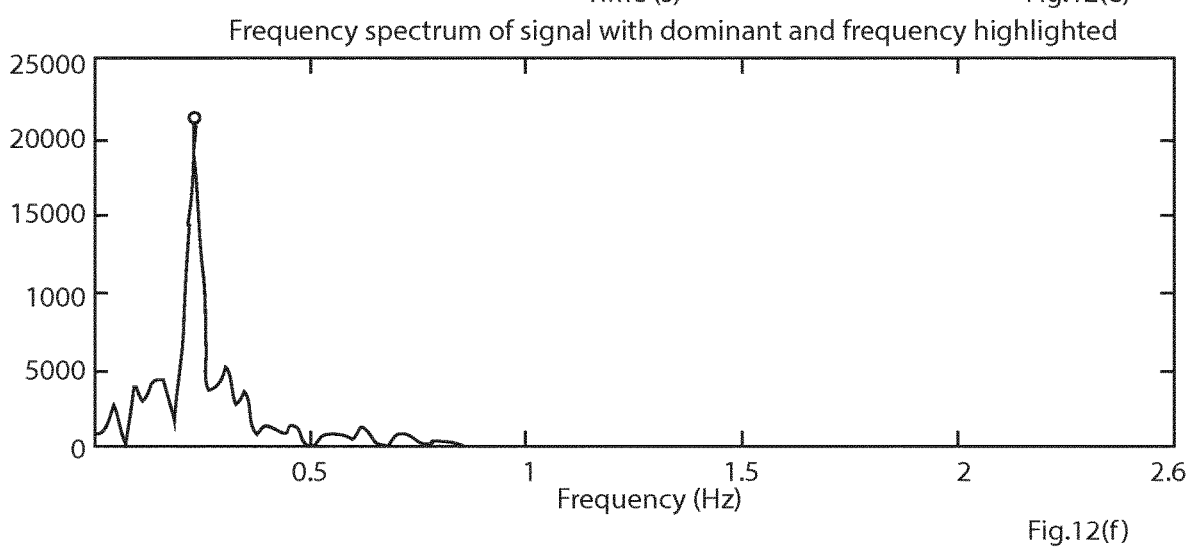

FIGS. 12(a) to 12(f) are plots of the main intermediate calculations from an implemented algorithm to determine the respiratory rate for a single transducer signal, as shown in FIG. 9. FIG. 12(a) shows the raw output from a single sensor over a 60 second time period showing the peaks and troughs indicative of normal breathing. One movement artefact can be seen as an increase in the signal strength at approximately second 35. After the motion artefact, a short sharp downward artefact can be seen. FIG. 12(b) shows the same signal with baseline correction and a moving average smoothing filter applied. The sharp downward spike is removed from the signal, but the large movement artefact remains. FIG. 12(c) shows the results from an artefact detection function. Where the black line is in the higher state, a large non-respiratory artefact has been determined to have occurred. Other artefact detection methods may be overlaid on this as required. FIG. 12(d) shows the same signal with the section designated as artefact smoothly removed from the waveform. Small downward troughs can be seen either side of the removed section. This area is flagged for the following step to ensure it does not interfere with the peak trough detection algorithm. FIG. 12(e) shows the signal in FIG. 12(d) with peaks and troughs identified by the system's processor. The area around the detected artefact is removed from consideration as it is not an accurate representation of the signal. FIG. 12(f) shows the frequency spectrum of the signal, with the most prominent signal highlighted at approximately 0.25 Hz, or 15 breaths per minute. The smooth removal of the artefact has resulted in a clearly discernable breathing frequency.

Figures 9A, 13A:
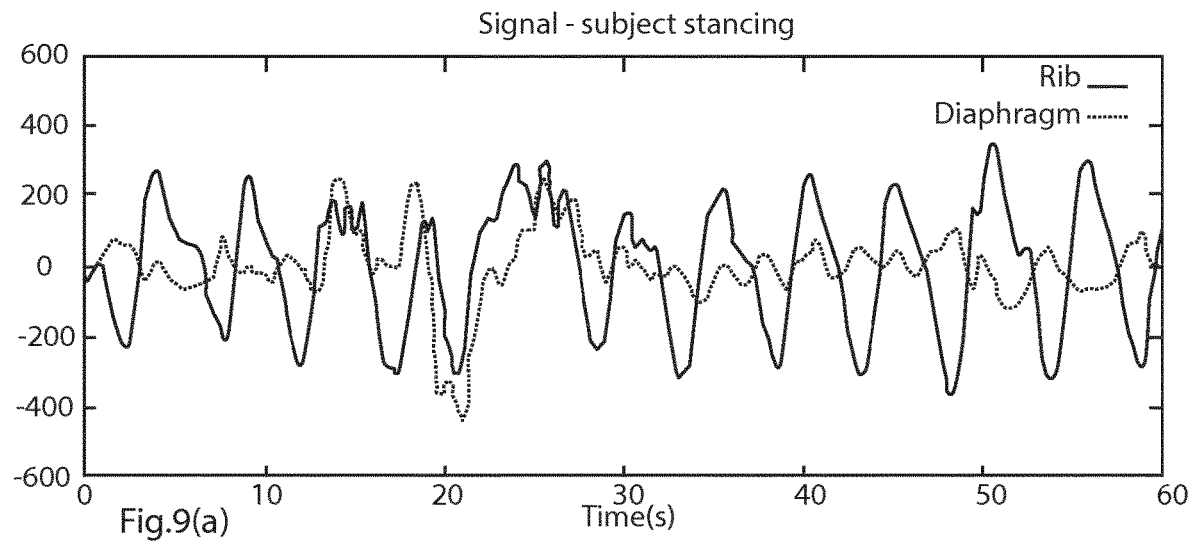
FIG. 13(a) shows signals for each channel representative of normal breathing over a 60 s period which has minimal movement artefact while the subject is standing.
Figures 9B, 13B:
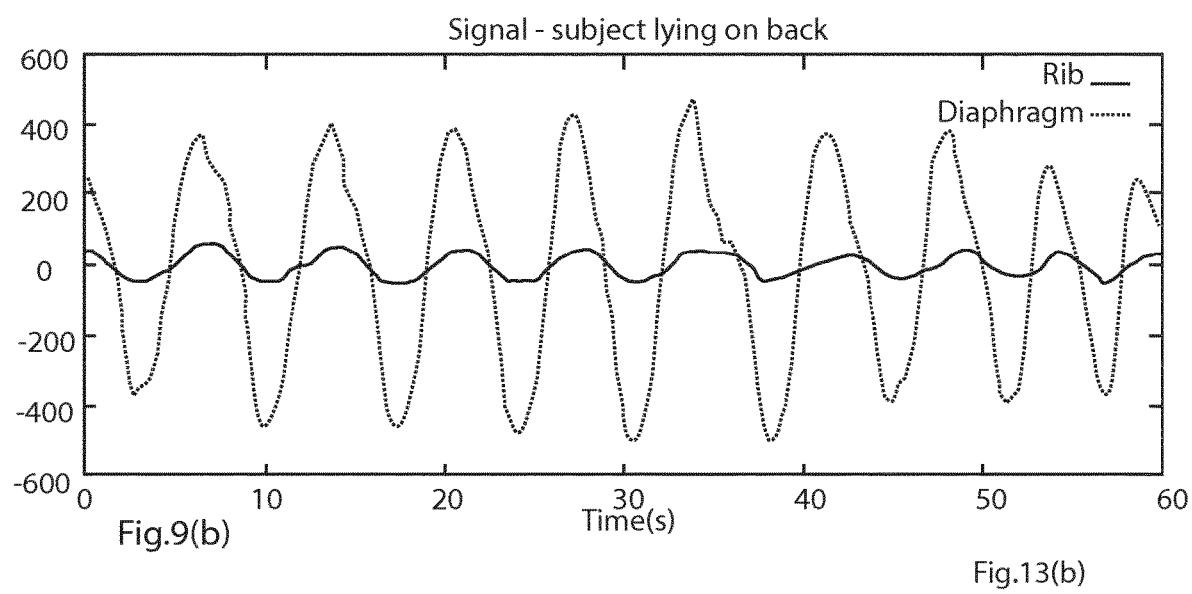
FIG. 13(b) shows the corresponding signal when the subject is lying on their back, again having a normalised numerical vertical axis and a time horizontal axis.

FIGS. 13(a) and 13(b) are plots showing examples of two different breathing regimes—rib breathing and diaphragm breathing. FIG. 13(a) shows the signals from the two transducers when the subject is standing up and predominantly rib breathing. A short movement artefact is visible around second 25. The diaphragm signal is much smaller and less coherent than the rib signal. Artefact detection will remove the diaphragm signal from consideration due to low signal strength. FIG. 12(b) shows a signal from the same subject when the subject is lying on their back and predominantly diaphragm breathing. In this case the rib signal is of low magnitude and will be rejected by the algorithm. It is important to note that these figures show the extremes of rib and diaphragm breathing and that normal breathing and differences from subject to subject will have a greater or lesser effect on each sensor.

Figure 14A:
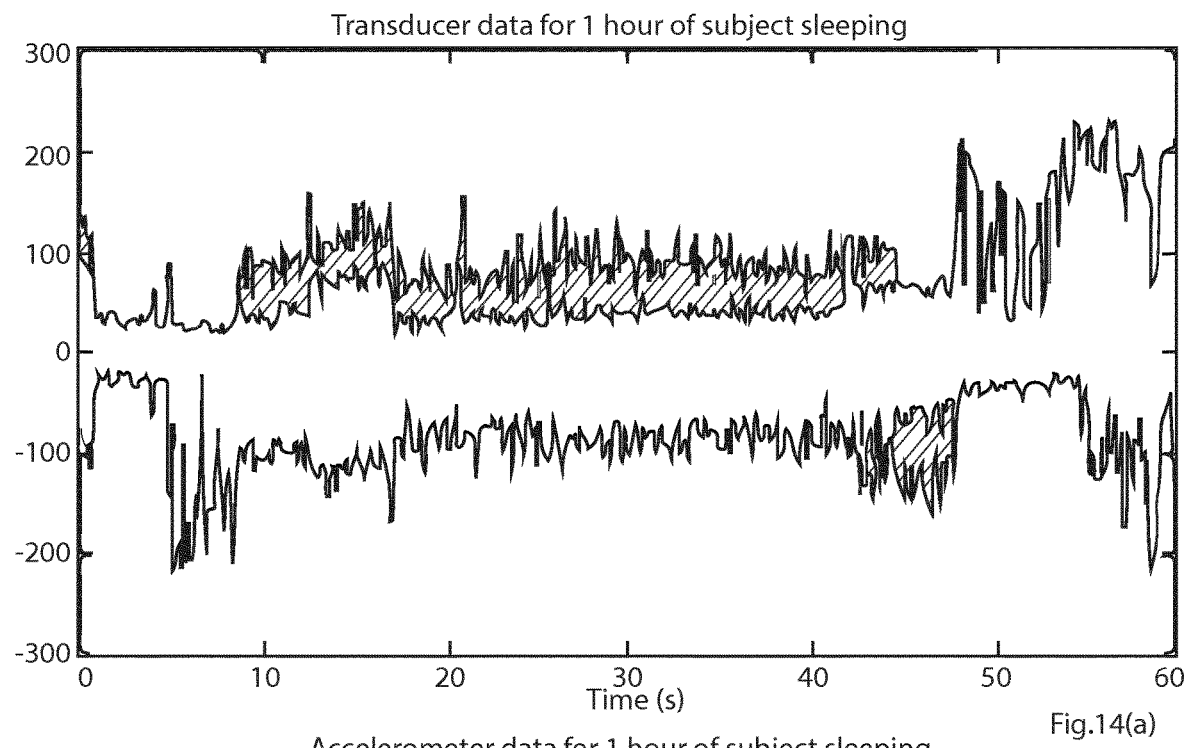
FIG. 14 (*a*) shows the signals from transducers over a period of 1 hour, collected when the subject was asleep.
Figure 14B:
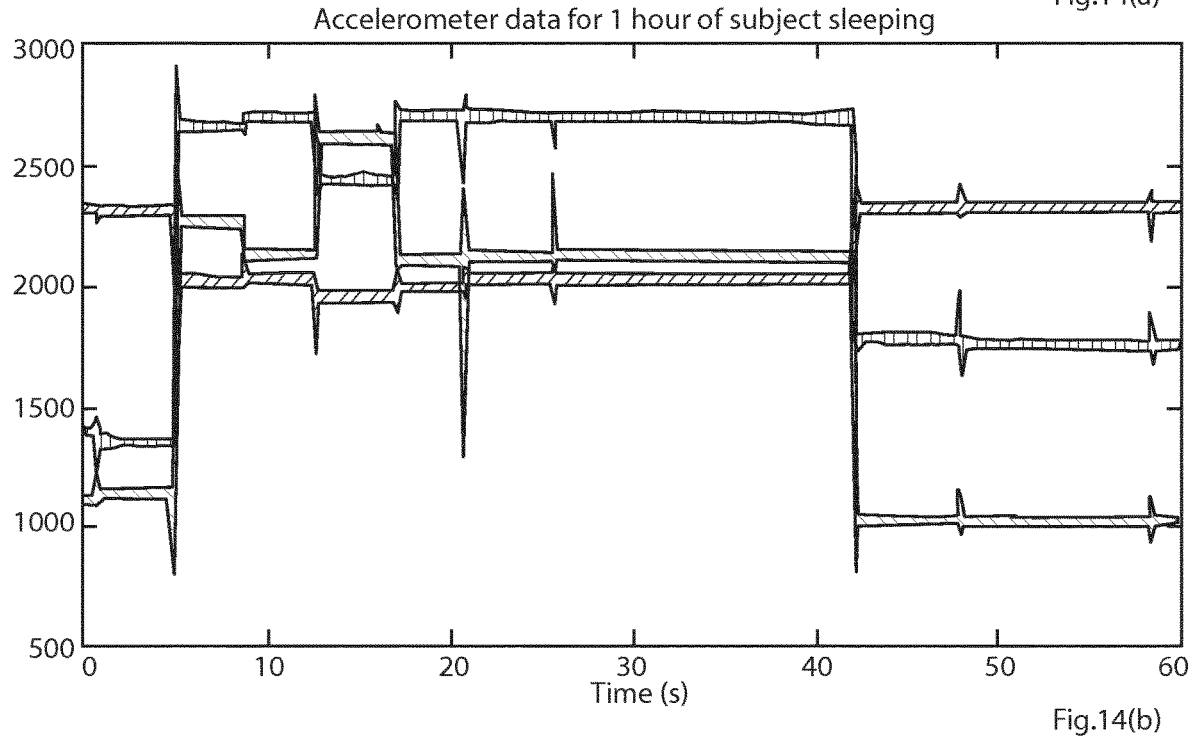

FIGS. 14(a) and 14(b) are plots showing the piezoelectric transducer and accelerometer signals for a subject sleeping over a period of one hour. Individual breaths are not discernable in FIG. 14(a) at this resolution. The upper and lower magnitudes of the transducers 5 and 6 are shown as solid lines. Transducer 6 is to the fore, and transducer 5 is to the rear and shown hatched. The magnitude of the signals can be seen to change at periods during the hours. Abrupt shifts in the subject's body position can be seen in FIG. 14(b) as jumps in the accelerometer signals, here moving from lying on the back, to lying on the side and then back again for the last 20 minutes. The subject can be seen to be nominally still for periods of up to 15 minutes between these movements.

The transducers transport the change in voltage through electrical contacts which have leads connecting the contacts of each movement transducer to the input electric contacts of the filter circuitry. Filtering circuitry is integrated on a printed circuit board upon which the amplifiers and the processor unit reside. All transportation of the signal from the filter pre-transmission is done on the PCB.

The processor 14 and/or other devices such as GPRS and Bluetooth radio respiratory sensor is stacked on top of the sensor element which is on the body. This is secured mechanically and offers easy connection and removal while ensuring a strong electric connection between both parts.

The preferred relative positions of the senor as shown in FIG. 5 on the $10^{th}$ rib is preferred, although the $7^{th}$ and $8^{th}$ may alternatively be used. This placement is the preferred location to utilise the mechanics of respiration. The ribcage, at the denoted location, is more flexible and subject to the largest deformations during respiratory effort. Where all parts of the thoracic region undergo fixed loci of displacement, the magnitude of displacement is relative to individual locations. The fundamental function of these mechanics is to create a vacuum within the thoracic cavity thus creating negative airspace to draw air into the lungs via nose or mouth. This is undertaken through two modes of operation which can be largely mutually exclusive.

The distending first operation triggers an involuntary contraction of the muscles around the ribcage, causing the rib cage to lift up. As the rib cage lifts up, it creates an increased internal volume in the thoracic cavity. This increase in volume also creates a vacuum. Air flows from positive pressure into negative pressure. Thus, air flows into the mouth and nose of a human subject and causes respiration to begin. Air is then pushed out by the muscles around the ribcage while relaxing, thus decreasing the internal volume of said cavity and pushing air out of the body. This is also aided by the diaphragm as it maintains a positive pressure upon the base of the lungs. This diaphragm is a muscle which divides the thoracic region from the abdominal region.

A distending second operation involves an increase in the internal volume of the abdomen region, which causes a negative pressure and thus draws down the diaphragm. By causing this, the internal volume of the thoracic region increases, thus creating a vacuum and drawing air in. Air is expelled when the volume of the abdomen cavity is decreased and the diaphragm is again pushed up against the lungs, decreasing the volume of the thoracic region and expelling air out.

The effect of the two operations attributed to respiratory effort is seen across the thoracic and abdominal region. It is effective to measure respiration at any location using the methodology as outlined by this invention of a plurality of sensors in a set configuration. However the preferred location as outlined in this invention is the most efficient area of measurement.

These two operations can act independently if negligible rib cage movement is ignored. More often these operations occur in parallel. Thus, to be able to measure both the thoracic and abdominal displacement in a single location is a significant advantage.

Further to the need to detect respiratory rate, the device can also detect with high accuracy the moments of inhalation and exhalation as show in FIG. 12(e), and the duration of each. Such application is highly sought after when monitoring lung capacity to ensure lung damage from over-pressurising the volume is not exceeded during invasive and/or non-invasive ventilation.

In embodiments which have one or more accelerometers, these are used to detect when movements occur and this information may be used to smooth or remove artefacts from the strain transducer signals. Artefact correction is applied to the strain transducer signal, and the processor does not assume that all artefacts are accounted for on the accelerometer—arm movements, direct contact with sensors etc. Also, the processor may use accelerometer orientation to weigh the relative usefulness of the two strain transducers (e.g. weight in favour of abdomen sensor when patient is lying down.

Some of the advantages of the invention may be summarised as:

(a) Improved accuracy by ensuring a superior method of sensor application to the wearer which does not require the wearer's assistance nor require the wearer to be assisted.

(b) By having both filtering and signal processing at the point of measurement improves accuracy due to reducing anxiety of the wearer and promoting longer continuous use, thereby improving analytics.

(c) It also reduces any effects of external influences such as electromagnetic interference from peripheral devices, unlike the prior art arrangements having lengthy wires promoting noise in the signal.

(d) Eliminating the majority of unwanted motion artefacts irrespective of placement within a preferred area of application.

(e) Reducing the effect of philological variances such as body mass index, body position, location, activity and condition again pre-processing to ensure high level of accuracy.

(f) Having a secure but removable fixing of the sensor and single construction enables reduction in cross contamination from device reuse which more efficient utilisation of higher end electronics.

(g) Having a profile and contour promotes easier cleaning.

(h) Having profile and contours that promote patient comfort and reduction from unintentional interference from moving limbs.

The invention is not limited to the embodiments described, but may be varied in construction and detail. For example the system may additionally include a gyroscope and the processor may process the gyroscope output by enabling the posture of the body to be known to the processor, thus enabling anomalies of the transducers to be accounted for.

The invention claimed is:

1. A respiration monitoring system comprising:
a flexible substrate,
an adhesive arranged on a surface of the flexible substrate to releasably adhere the flexible substrate to a patient's torso,
a plurality of embedded deformation transducers fixed to said flexible substrate including at least a first transducer and a second transducer,
the first transducer and the second transducer being located on the substrate at an angle relative to an apex formed at a mutual location on the substrate, the first transducer and the second transducer having a size and the mutual location on the substrate so that simultaneously the first transducer is configured to overlie at least part of the patient's 10th rib and the second transducer is configured to overlie at least part of the patient's 11th rib or abdomen so that the apex defined by said mutual location of said first transducer and said second transducer is configured to be pointed rearward and downward with respect to the patient,
the transducers being positioned on the substrate to enable measuring both thoracic and abdominal displacement in a single location,
an electronic controller releasably mounted on the substrate, the electronic controller being positioned on a same side of both the first transducer and the second transducer,
the electronic controller receiving signals by conductors from the first transducer and the second transducer, and
an accelerometer producing an output signal representative of a posture of the patient's torso, and
the electronic controller is configured to receive signals from the first transducer and the second transducer and to compensate for motion noise based on the output signal from the accelerometer, and to thereby derive an output representative of respiration based upon the signals from the first transducer and the second transducer.

2. The system as claimed in claim 1, wherein said first and second transducers are arranged on the substrate at a mutual acute angle.

3. The system as claimed in claim 2, wherein said angle is in the range of 20° to 80°.

4. The system as claimed in claim 1, wherein the system comprises a unitary sensor for adhering to the patient's skin, said sensor including:
the substrate with the deformation transducers, and
the electronic controller,
and wherein the electronic controller is included in a housing on the substrate with a signal conditioning circuit, and
wherein the electronic controller housing is releasably mounted on the substrate.

5. The system as claimed in claim 1, wherein the deformation transducers include at least two strain transducers.

6. The system as claimed in claim 1, wherein the electronic controller is configured to trigger an artefact detection algorithm at regular intervals in which signals which are outside predetermined limits of measurement are removed.

7. The system as claimed in claim 1, wherein the electronic controller is configured to execute, when determining respiration rate, a frequency domain algorithm or a time domain algorithm.

8. The system as claimed in claim 1, wherein the electronic controller is configured to execute, when determining respiration rate, a frequency domain algorithm to take accelerometer data from the accelerometer as a secondary input and to compensate for cyclical interference from the patient or environment such as walking, by extracting frequency domain information from the accelerometer data.

9. The system as claimed in claim 1, wherein the electronic controller is configured to, when determining respiration rate, execute a frequency domain algorithm to take accelerometer data from the accelerometer as a secondary input and to compensate for cyclical interference from the patient or environment such as walking, by extracting frequency domain information from the accelerometer data, and
wherein the electronic controller is configured to detect and compensate for movements using the accelerometer data.

10. The system as claimed in claim 1, wherein the electronic controller is configured to produce a waveform represented by a repeating pattern of peaks and troughs at a rate indicative of the respiratory rate of the patient.

11. The system as claimed in claim 10, wherein the electronic controller is configured to produce the waveform for diagnosis of apnea events in sleeping subjects by detecting portions of the waveform indicative of an apnea event.

12. The system as claimed in claim 1, wherein the electronic controller is configured to receive a unique identifier for a use with a particular subject, and to discontinue or erase said identifier upon removal of the substrate from the particular subject and/or re-charging for a next use.

13. A method of monitoring respiration of a human subject using a system comprising:
a flexible substrate,
an adhesive arranged on a surface of the flexible substrate to releasably adhere the flexible substrate to a patient's torso,
a plurality of embedded deformation transducers fixed to said flexible substrate including at least a first transducer and a second transducer,
the first transducer and the second transducer being located on the substrate at an angle relative to an apex formed at a mutual location on the substrate, the first transducer and the second transducer having a size and the mutual location on the substrate so that simultaneously the first transducer overlies at least part of a patient's 10th rib and the second transducer overlies at least part of a patient's 11th rib or abdomen so that the apex defined by said mutual location of said first transducer and said second transducer is pointed rearward and downward with respect to the patient,
the transducers being positioned on the substrate to enable measuring both thoracic and abdominal displacement in a single location,
an electronic controller releasably mounted on the substrate, the electronic controller being positioned on a same side of both the first transducer and the second transducer,
the electronic controller receiving signals by conductors from the first transducer and the second transducer, and
an accelerometer producing an output signal representative of a posture of the patient's torso, and
the electronic controller is configured to receive signals from the first transducer and the second transducer and to compensate for motion noise based on the output signal from the accelerometer, and to thereby derive an output representative of respiration based upon the signals from the first transducer and the second transducer,
the method comprising the steps of:
adhering the substrate to the patient so that the first transducer substantially overlies the patients 10th rib and the second transducer overlies the patient's 11th rib or the abdomen of the patient, and
the electronic controller processing signals from the transducers to derive the output representative of respiration of the patient including compensating for motion noise based on the output signal from the accelerometer, in which the electronic controller processes data from the first transducer as being primarily representative of rib distending respiration and from the second transducer as being primarily representative of either diaphragm respiration or patient motion artefact.

14. The method as claimed in claim 13, wherein the electronic controller automatically decides on what the deformation of the second transducer represents according to a signal from an auxiliary sensing device.

15. The method as claimed in claim 14, wherein the system includes the accelerometer as the auxiliary sensing device, and:
the electronic controller automatically decides on what the deformation of the second
transducer represents according to the output signal from the accelerometer.

16. The respiration monitoring system of claim 1, wherein the first transducer and the second transducer are of equal length, width, thickness and composition.

17. The respiration monitoring system of claim 1, wherein the electronic controller is connected to the flexible substrate via a hook and loop connection.

18. The system as claimed in claim 1, wherein the electronic controller is configured to execute, when determining respiration rate, a time domain algorithm comprising producing a waveform represented by a repeating pattern of peaks and troughs at a rate indicative of the respiratory rate of the patient, and detecting a distance between the peaks and a distance between the troughs in the waveform to derive the respiration rate.

* * * * *